United States Patent
Dooley et al.

(10) Patent No.: US 6,292,050 B1
(45) Date of Patent: Sep. 18, 2001

(54) CURRENT AND TEMPERATURE COMPENSATED VOLTAGE REFERENCE HAVING IMPROVED POWER SUPPLY REJECTION

(75) Inventors: Michael W. Dooley, St. Paul; Terrence L. Marshall, Minneapolis; William J. Linder, Golden Valley; Suneel Arora, Minneapolis, all of MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/260,206

(22) Filed: Mar. 1, 1999

Related U.S. Application Data

(63) Continuation-in-part of application No. 08/790,470, filed on Jan. 29, 1997, now abandoned.

(51) Int. Cl.$^7$ ...................................................... G05F 1/10
(52) U.S. Cl. ........................................... 327/540; 327/545
(58) Field of Search .................................. 327/538–541, 327/545; 323/312, 315

(56) References Cited

U.S. PATENT DOCUMENTS

| | | | |
|---|---|---|---|
| 3,103,617 | 9/1963 | Schneider et al. | 323/22 |
| 3,300,658 | 1/1967 | Slusher | 307/88.5 |
| 4,733,160 | 3/1988 | Draxelmayr | 323/314 |
| 4,769,589 | 9/1988 | Rosenthal | 323/313 |
| 4,868,416 | * 9/1989 | Fitzpatrick et al. | 323/313 |
| 4,873,490 | 10/1989 | Hecht et al. | 328/3 |
| 4,917,093 | 4/1990 | Dufresne et al. | 128/421 |
| 5,030,849 | 7/1991 | Brokaw | 307/310 |
| 5,061,862 | * 10/1991 | Tamagawa | 323/312 |
| 5,159,520 | 10/1992 | Toyooka et al. | 361/103 |
| 5,220,273 | 6/1993 | Mao | 323/313 |
| 5,323,068 | 6/1994 | Freitas | 307/455 |
| 5,372,605 | 12/1994 | Adams et al. | 607/5 |
| 5,387,228 | 2/1995 | Shelton | 607/11 |
| 5,670,868 | 9/1997 | Moriguchi et al. | 323/313 |
| 5,797,967 | 8/1998 | KenKnight | 607/4 |
| 5,818,212 | * 10/1998 | Min et al. | 323/314 |
| 5,841,270 | 11/1998 | Do et al. | 323/314 |
| 5,929,616 | 7/1999 | Perraud et al. | 323/274 |
| 6,034,391 | 3/2000 | Tobita | 257/306 |
| 6,046,578 | 4/2000 | Feldtkeller | 323/314 |
| 6,124,754 | 9/2000 | Afghani | 327/538 |
| 6,150,871 | 11/2000 | Yee | 327/538 |
| 6,172,555 | 1/2001 | Gusinov | 327/539 |
| 6,181,196 | 1/2001 | Nguyen | 327/539 |

FOREIGN PATENT DOCUMENTS

| | | |
|---|---|---|
| 0360551 | 3/1990 | (EP) . |
| 98/32490 | 7/1998 | (WO) . |

\* cited by examiner

*Primary Examiner*—Kenneth B. Wells
(74) *Attorney, Agent, or Firm*—Schwegman, Lundberg, Woessner & Kluth, P.A.

(57) ABSTRACT

A current and temperature compensated voltage reference circuit uses a power supply voltage as low as 1.3 Volts. A folded-cascode amplifier measures the temperature dependent voltages provided by first and second bias circuits, each including two series-coupled diodes or diode-connected bipolar junction transistors (BJTs), and provides a resulting proportional to absolute temperature (PTAT) current through a cascode-protected output transistor. A voltage reference circuit uses a PTAT current through a resistor to create a PTAT voltage in series with a diode-voltage. The resistor value is adjusted until the sum of these voltages is equal to the bandgap voltage of silicon, providing a temperature compensated voltage reference. The reference circuit is suitable for use with an implantable cardiac rhythm management system having a battery that provides a power supply voltage varying approximately between 1.3 Volts and 3.25 Volts. Cascode-protected current mirrors further improve rejection of such variations in the power supply voltage.

53 Claims, 10 Drawing Sheets

CURRENT AND TEMPERATURE COMPENSATED VOLTAGE REFERENCE HAVING IMPROVED POWER SUPPLY REJECTION

CROSS-REFERENCE TO RELATED APPLICATION

This application a continuation-in-part of U.S. patent application Ser. No. 08/790,470 entitled, "CURRENT AND TEMPERATURE COMPENSATED VOLTAGE REFERENCE," filed on Jan. 29, 1997, now abandoned which assigned to the assignee of the present application, and which is incorporated herein by reference.

FIELD OF THE INVENTION

This invention relates generally to precision voltage and current references and particularly, but not by way of limitation, to a system that includes a temperature dependent current source used to generate a temperature compensated voltage reference in a cardiac rhythm management system.

BACKGROUND

Many integrated circuit functions require precise voltage and current references. For example, an analog-to-digital converter typically requires a precise voltage reference to establish and quantize an analog input voltage range. In another example, many analog filters, such as transconductance-capacitance ($g_mC$) filters, have filter gain and rolloff frequency characteristics that depend upon their bias currents. A precise current reference is useful for generating accurate bias currents in such filters and other circuits.

Many battery powered electronics applications, including implantable cardiac rhythm management systems, need current and temperature compensated voltage reference circuits that operate at low power supply voltages and power consumption. There is a critical need for circuits, including reference circuits, that operate at low power supply voltages and draw less current from the low voltage power supply in order to increase battery longevity. There is also a need for such reference circuits in which the value of the reference voltage and reference current are capable of fine adjustment. There is a further need for such reference circuits in which the resulting reference voltage is temperature compensated, i.e. the sensitivity of the reference voltage to temperature variations is reduced. Moreover, the internal impedance of the battery results in variations of the terminal voltage. When significant current is being drawn from the battery, the terminal voltage of the battery can droop significantly. There is a need for a reference circuit that can accommodate such power supply voltage variations.

SUMMARY

The present system provides a system that includes a current and temperature compensated voltage reference that is capable of operating from a power supply voltage as low as approximately 1.3 Volts, and that provides improved power supply rejection. For battery powered electronics applications, operation at lower power supply voltages offers significant advantages; it may eliminate the need for electrically coupling more than one battery in series in order to obtain a higher power supply voltage. Also, in some batteries, an internal battery impedance increases over the course of the battery life, thereby reducing the voltage available at the battery terminals. Thus, the useful life of the battery may be extended by using a reference circuit that is capable of operating from this reduced battery terminal voltage near the end of the battery's life or when significant currents are being drawn from the battery. The reference circuit should be capable of accommodating such variations in the power supply voltage.

These characteristics are particularly desirable for implantable medical devices, including cardiac rhythm management systems, such as pacemakers and defibrillators, in which circuits that are capable of operating at reduced power supply voltages can extend battery life for several years, thereby avoiding surgical explantation and replacement of the implanted device. In elderly patients, such traumatic surgical intervention may be both uncomfortable and risky.

The system, by operating from a power supply voltage as low as approximately 1.3 Volts and providing improved power supply rejection, may significantly increase the longevity of the implanted device. The system also operates with less power consumption, further increasing the longevity of the implanted device. The increased device longevity provides the implanting physician with more options in selecting the most appropriate therapy for the patient. Discomfort and patient mortality due to explantation and replacement of the implanted medical device may be decreased. The system also provides a reference circuit in which the value of the reference voltage and reference current are capable of fine adjustment. The resulting reference voltage is temperature compensated, i.e. the sensitivity of the reference voltage to temperature variations is reduced. Furthermore, improved power supply rejection better accommodates variations in the power supply voltage.

In one embodiment, the system includes a reference circuit. The reference circuit includes first and second bias circuits and a complementary metal oxide semiconductor (CMOS) differential input first amplifier. The first bias circuit includes less than three series-coupled diodes comprising first and second series-coupled diodes biased by at least one first current source, providing a first temperature dependent voltage across the series-combination of the first and second diodes. The second bias circuit includes a resistor and less than three series-coupled diodes comprising third and fourth series-coupled diodes biased by at least one second current source, providing a second temperature dependent voltage across the series-combination of the third and fourth diodes, wherein the second temperature dependent voltage has a different temperature dependence than the first temperature dependent voltage. The first amplifier includes first and second inputs electrically coupled to the respective first and second temperature dependent voltages of the respective first and second bias circuits, and having an output providing a proportional to absolute temperature (PTAT) reference current through the resistor by measuring a difference between the first and second temperature dependent voltages. A power supply voltage provided to the first amplifier is between 1.3 volts and 2.1 volts.

In another embodiment, a cardiac rhythm management system includes a battery, an electronics circuit, for controlling delivery of cardiac therapy to a patient, and a reference circuit. The reference circuit is electrically coupled to the battery for receiving a first power supply voltage therefrom, and electrically coupled to a second power supply voltage. The reference circuit provides a reference voltage to the electronics circuit. The reference circuit operates from the first power supply voltage that is as low as 1.3 Volts. The reference circuit includes an amplifier, a first bias circuit, at least one first current source, a second bias circuit, and at least one second current source. The first bias circuit includes less than three series-coupled diodes comprising first and second series-coupled diodes. The first bias circuit is coupled to the second power supply voltage and includes a first output voltage terminal. The at least one first current source is coupled in series between the first power supply voltage and the first output voltage terminal. The second bias circuit includes less than three-series-coupled diodes comprising third and fourth series-coupled diodes. The second bias circuit is coupled to the second power supply voltage and includes a second output voltage terminal. The at least one second current source is coupled in series between the first power supply voltage and the second output voltage terminal.

In another embodiment, the system includes a reference circuit that includes a first bias circuit, a second bias circuit, a CMOS differential-input folded cascode first amplifier, and a voltage reference circuit. The first bias circuit has a first temperature dependence and includes less than three series-coupled diodes comprising first and second diodes that are series-coupled with each other and biased by at least a first current source. The first bias circuit provides a first temperature dependent voltage across the series combination of the first and second series-coupled diodes. The second bias circuit includes a resistor and less than three series-coupled diodes comprising third and fourth diodes. The third and fourth diodes are series-coupled with each other and biased by at least a second current source. The second bias circuit provides a second temperature dependent voltage across the series combination of the third and fourth series-coupled diodes. The second temperature dependent voltage has a different temperature dependence than the first temperature dependent voltage. The first amplifier receives a power supply voltage that is between 1.65 Volts and 2.1 Volts. The first amplifier has first and second inputs electrically coupled to the respective first and second bias circuits, and has an output providing a proportional to absolute temperature reference current through the resistor by measuring a difference between the first and second temperature dependent voltages. The voltage reference circuit receives a current proportional to the reference current, and provides a temperature-compensated reference voltage that is based on a series-combination of third and fourth voltages. The current proportional to the reference current establishes the third voltage having a temperature dependence that substantially offsets the temperature dependence of the fourth voltage to provide the reference voltage.

In another embodiment, the system includes a method. A first bias circuit, consisting essentially of first and second diodes that are series-coupled with each other, is biased with a first current to establish a first temperature dependent voltage. A second bias circuit, consisting essentially of a resistor and third and fourth diodes, the third and fourth diodes being series-coupled with each other, is biased with a second current to establish a second temperature dependent voltage. A voltage difference is measured between the first and second temperature dependent voltages. A proportional to absolute temperature reference current is generated based on the voltage difference.

In another embodiment, the system includes a reference circuit. The reference circuit includes a first power supply providing a voltage that is between 1.3 volts and 2.1 volts. The reference circuit also includes a first bias circuit including less than three series-coupled diodes comprising first and second series-coupled diodes biased by at least one first current source, providing a first temperature dependent voltage across the series-combination of the first and second series-coupled diodes. The reference circuit also includes a second bias circuit including less than three series-coupled diodes comprising a resistor, and also comprising third and fourth series-coupled diodes biased by a second current source, providing a second temperature dependent voltage across the third and fourth series-coupled diodes, wherein the second temperature dependent voltage has a different temperature dependence than the first temperature dependent voltage. The reference circuit also includes a complementary metal-oxide-semiconductor (CMOS) differential input first amplifier.

The first amplifier includes a first input transistor, having a drain and a source, and having a gate coupled to the first bias circuit. A second input transistor has a drain, a source coupled to the source of the first input transistor, and a gate coupled to the second bias circuit. A first load transistor has a source coupled to the first power supply, a drain coupled to the drain of the first input transistor, and a gate. A second load transistor has a source coupled to the first power supply, a drain coupled to the drain of the second input transistor, and a gate coupled to the gate of the first load transistor. A first load cascode transistor has a source coupled to the drain of the first load transistor, a drain, and a gate coupled to the gate of the first load transistor. A second load cascode transistor has a source coupled to the drain of the second load transistor, a drain, and a gate coupled to the gate of the second load transistor. A third load transistor has a drain coupled to the drain of the first load cascode transistor, a gate, and a source coupled to a second power supply. A fourth load transistor has a drain coupled to the drain of the second load cascode transistor, a gate, and a source coupled to the second power supply. An output transistor has a source coupled to the first power supply, a drain, and a gate coupled to the drain of the first load cascode transistor.

In another embodiment, the system includes a reference circuit including a first bias circuit, a second bias circuit, a folded cascode complementary metal-oxide-semiconductor (CMOS) differential input first amplifier, a cascode-protected current source, and a voltage reference circuit. The first bias circuit includes less than three series-coupled diodes comprising first and second series-coupled diodes biased by a first current source, providing a first temperature dependent voltage across the series-combination of the first and second series-coupled diodes. The second bias circuit includes a resistor and also includes less than three series-coupled diodes comprising third and fourth series-coupled diodes biased by a second current source, providing a second temperature dependent voltage across the series-combination of the third and fourth series-coupled diodes. The second temperature dependent voltage has a different temperature dependence than the first temperature dependent voltage. The first amplifier receives a power supply voltage approximately between 1.3 Volts and 2.1 Volts, and has first and second inputs electrically coupled to the respective first and second bias circuits, and has an output transistor providing a proportional to absolute temperature (PTAT) reference current through the resistor by measuring a difference between the first and second temperature dependent voltages. The cascode-protected current source provides a current substantially proportional to the reference current. A voltage reference circuit receives the current substantially proportional to the reference current from the cascode-protected current source, and provides a first voltage having a temperature dependence that substantially offsets the temperature dependence of a second voltage in series with the first voltage to provide a resulting temperature compensated reference voltage. Other aspects of the invention will be apparent on reading the following detailed description of the invention and viewing the drawings that form a part thereof.

BRIEF DESCRIPTION OF THE DRAWINGS

In the drawings, like numerals describe substantially similar components throughout the several views.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description is, therefore, not to be taken in a limiting sense, and the scope of the present invention is defined by the appended claims and their equivalents.

Figure 1:
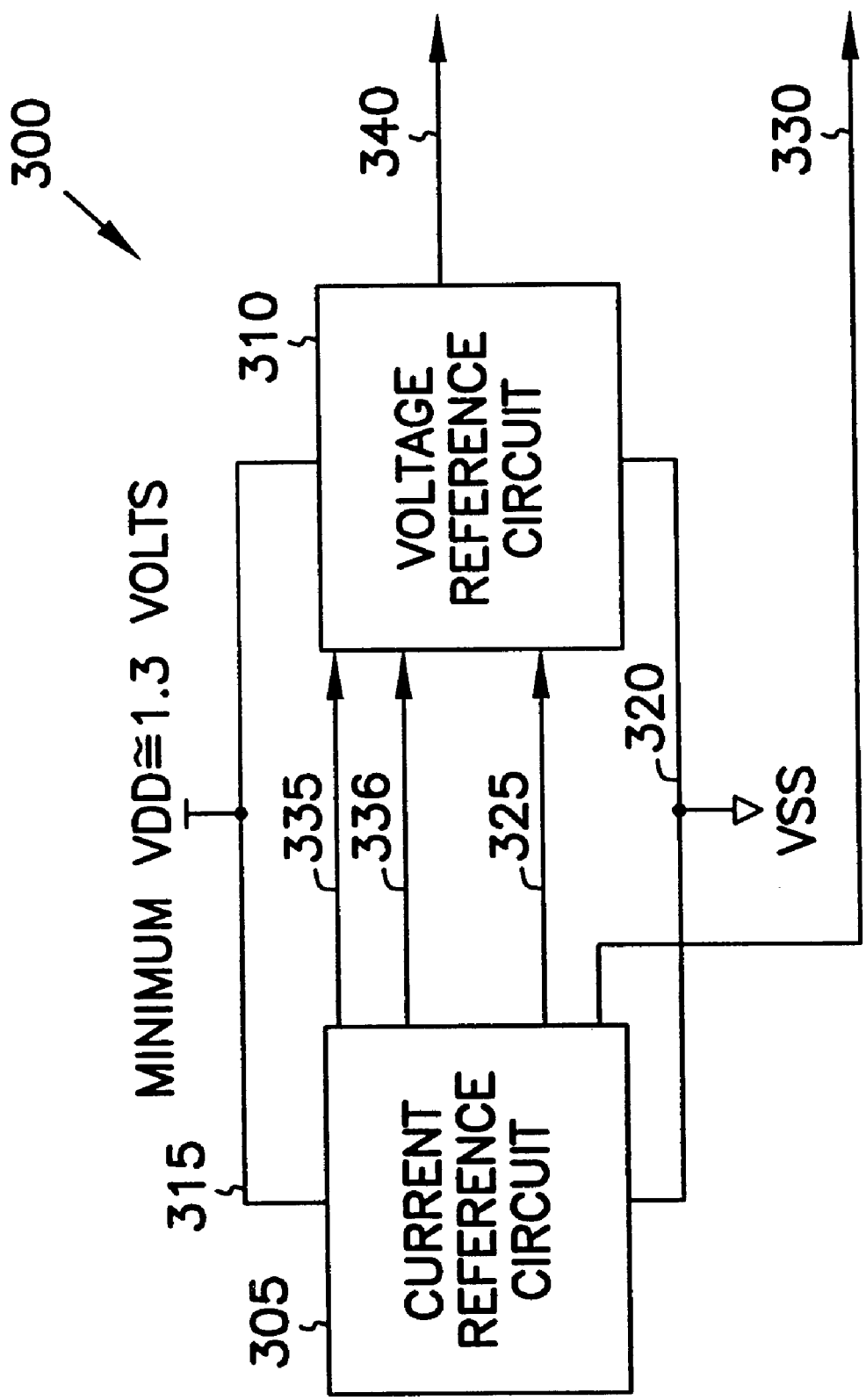
FIG. 1 is a schematic illustration of a reference circuit including a current reference circuit and a voltage reference circuit.

FIG. 1 is a schematic illustration of one embodiment of the system providing a silicon integrated circuit (IC) reference circuit 300 including current reference circuit 305 and voltage reference circuit 310, each receiving a power supply voltage $V_{DD}$ at power supply node 315 and a ground voltage $V_{SS}$ at ground voltage node 320. Current reference circuit 305 provides an internal reference current, as discussed below, and provides a voltage at node 325 from which a current proportional to the reference current can be generated in voltage reference circuit 310. Current reference circuit 305 is capable of providing a current proportional to the reference current through node 330. Current reference circuit 305 also provides through node 335 a first bias voltage to voltage reference circuit 310 for biasing an amplifier input therein. Current reference circuit 305 also provides through node 336 a fourth bias voltage to voltage reference circuit 310 for biasing current mirrors therein. Voltage reference circuit 310 provides a reference voltage at node 340.

Figure 2:
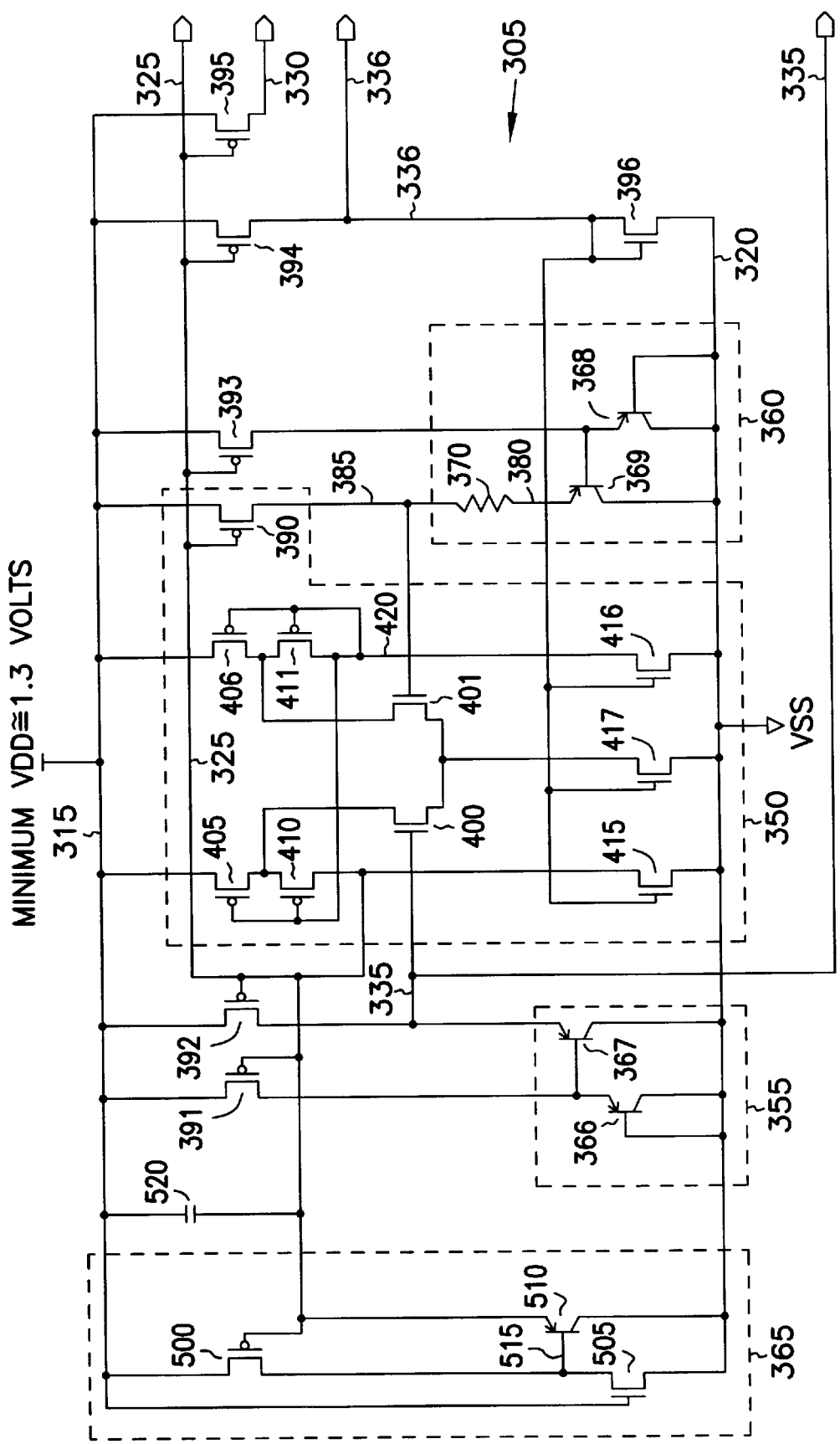
FIG. 2 is a more detailed schematic illustration of the current reference circuit of FIG. 1.

FIG. 2 is a more detailed schematic illustration of one embodiment of current reference circuit 305. In FIG. 2, current reference circuit 305 comprises first amplifier 350, first bias network 355, second bias network 360, and startup circuit 365. First bias network 355 includes two series-coupled diodes 366 and 367, implemented as base-emitter (BE) junctions of bipolar junction transistors (BJTs), each BJT receiving an independent collector-emitter current, $I_{CE}$, as described below. Second bias network 360 includes two series-coupled diodes 368 and 369, implemented as BE junctions of BJTs, each BJT receiving an independent $I_{CE}$, as described below. Second bias network 360 also includes first resistor 370 in series with the two series-coupled diodes, 368 and 369, therein.

The BE junction areas of the diodes 368 and 369 in the second bias network 360 are different from the BE junction areas of the diodes 366 and 367 in the first bias network 355. In one embodiment, the BE junction areas of the diodes 368 and 369 in the second bias network 360 are made four times larger than the BE junction areas of the diodes 366 and 367 in the first bias network 355. Each of the diodes 368 and 369 is implemented as four parallel-connected BJT's of the same area as the single BJT's that implement the diodes 366 and 367. Other BE junction area ratios and connection configurations could also be used without departing from the scope and spirit of the present invention.

Substantially identical $I_{CE}$ currents are provided to each of diodes 366, 367, 368, and 369. Since diodes 368 and 369 in second bias circuit 360 each have four times larger BE junction area than each of diodes 366 and 367 in first bias circuit 355, diodes 368 and 369 in second bias circuit 360 each have approximately one fourth the current density of diodes 366 and 367 in first bias circuit 355, as a result of the substantially identical $I_{CE}$ currents.

First bias network 355 provides at node 335 to a first input of first amplifier 350 the first bias voltage having a first temperature dependence resulting from the two series-coupled diodes, 366 and 367, therein. Second bias network 360 provides across its two series-coupled diodes, 368 and 369, a second bias voltage, having a second temperature dependence, at node 380, which is coupled through first resistor 370 to the output and the second input at node 385 of first amplifier 350.

First amplifier 350 measures the voltage difference, at nodes 335 and 385, between the first and second bias networks 355 and 360, providing in response thereto a reference current, $I_{PTAT}$, through first resistor 370, that is proportional to absolute temperature (PTAT). The value of $I_{PTAT}$ is illustrated by Equation (1).

$$I_{PTAT} = \frac{NV_T \times \ln(M)}{R_{370}} \quad (1)$$

In Equation (1), the value of reference current $I_{PTAT}$ is determined from: the number, N, of diodes connected in series in each of first and second bias circuits, 355 and 360, in this case N=2; the thermal voltage, $V_T$, which is approximately 0.0267 Volts at 37 degrees Celsius and is proportional to absolute temperature; the resistance value $R_{370}$ of first resistor 370, and the argument M of the natural logarithm, which is equal to the ratio of current densities in the diodes 366 and 367 in first bias network 355 to the current densities in the diodes 368 and 369 in second bias network 360, in this case M=4. In one embodiment, first resistor 370 is a variable or trimmable resistor having an adjustable resistance value $R_{370}$ near approximately 1.482 megaohms for adjusting reference current $I_{PTAT}$ to 50 nA at 37 degrees Celsius, or other fine adjustment to a desired value at a particular temperature.

The first bias voltage at node 335, the fourth bias voltage at node 336, and a voltage at node 325 from which reference current $I_{PTAT}$ is generated by output transconductor 390 of first amplifier 350, are each provided to voltage reference circuit 310. The voltage at node 325, from which reference current $I_{PTAT}$ is generated, is also provided to startup circuit 365 and to each of current mirror p-channel field-effect transistors PFETs 391–395. Current mirror PFETs 391–393 provide a $I_{CE}$ currents, proportional to reference current, $I_{PTAT}$, to respective diodes 366–368. Output transconductor PFET 390 of first amplifier 350 provides the reference current, $I_{PTAT}$, as the $I_{CE}$ current of diode 369. Current mirror PFET 394 provides a current, proportional to reference current $I_{PTAT}$, to diode-connected transistor 396, which generates the fourth bias voltage at node 336 in response thereto. The fourth bias voltage at node 336 is also provided to first amplifier 350 for biasing the gate terminals of current mirror n-channel field-effect transistors (NFETs) 415–417 contained therein. Current mirror PFET 395 is optionally included for providing a bias current at node 330, such as to another circuit on the integrated circuit. Other current mirror PFETs may similarly be used to provide other bias current sources to other circuits. Also, current mirror NFETs, having a gate terminal electrically coupled to node 336 and a source terminal electrically coupled to ground node 320, may be used to provide bias current sinks to other circuits.

In one embodiment, first amplifier 350 is a folded cascode amplifier that is carefully designed to operate from a reduced power supply voltage $V_{DD}$ at power supply node 315, such as a power supply voltage $V_{DD}$ as low as approximately 1.3 Volts, when biased by first and second bias circuits, 355 and 360. This allows reference circuit 300 to operate at a reduced power supply voltage $V_{DD}$, such as, for example, a voltage approximately between 1.3 Volts and 3.25 Volts provided by a single lithium-silver vanadium pentoxide battery cell in an implantable defibrillator. In another example, reference circuit 300 is operated from a power supply voltage $V_{DD}$ approximately between 1.65 Volts and 3.25 Volts. Thus, operation at a low power supply voltage, $V_{DD}$, is particularly advantageous for battery powered electronics devices, such as portable electronics or implantable electronics, but operation at higher values of power supply voltage $V_{DD}$ is also possible.

Folded cascode first amplifier 350 comprises source-coupled input NFETs 400 and 401, having respective gate terminals electrically coupled to the first and second bias circuits 355 and 360. The drain terminals of input NFETs 400 and 401 are respectively coupled to the drain terminals of load PFETs 405 and 406, the source terminals of which are electrically coupled to power supply node 315. Cascode PFETs 410 and 411 are each electrically coupled at their respective source terminals to the drain terminals of respective load PFETs 405 and 406. The drain terminals of cascode PFETs 410 and 411 are respectively electrically coupled to drain terminals of current mirror NFETs 415 and 416 at respective nodes 325 and 420.

Current mirror NFET 417 is electrically coupled at its drain terminal to the source terminals of each of input NFETs 400 and 401. The source terminals of each of current mirror NFETs 415–417 are coupled to ground node 320. The gate terminals of each of load PFETs 405 and 406 and cascode PFETs 410 and 411 are coupled to node 420, with cascode PFET 411 being diode-connected, i.e. the gate and drain terminals of cascode PFET 411 are both connected to node 420. Output transconductor 390 is a PFET having a gate terminal electrically coupled to node 325, a source terminal electrically coupled to power supply node 315, and a drain terminal electrically coupled to the second bias circuit 360 at node 385.

In order to obtain the above-described operation at reduced power supply voltages $V_{DD}$, first amplifier 350 must be carefully designed and biased. In one embodiment, input NFETs 400 and 401 are sized for operation in the weak inversion region. Current mirror NFETs 415–417 and load PFETs 405 and 406 are sized for operation in the moderate inversion region, i.e. between the weak inversion and strong inversion regions. Cascode PFETs 410 and 411 are sized for operation in the weak inversion region, and more particularly, cascode PFETs 410 and 411 are sized for operation at much lower current densities than load PFETs 405 and 406. Current density, J, through a field-effect transistor (FET) is illustrated in Equation (2)

$$J = I \times \frac{L}{W} \quad (2)$$

In Equation (2), current density J is determined from: the current I through the FET, L is the length of the FET between its drain and source regions, and W is the width of the FET in a direction transverse to the current flow between the drain and source regions.

In one embodiment, the dimensions, L and W, and bias currents, I, in the cascode PFETs 410 and 411 and load PFETs 405 and 406 are designed such that the load PFETs 405 and 406 have approximately between six and seven hundred times the current density J as in the cascode PFETs 410 and 411. At the bias point of first amplifier 350, i.e. nodes 335 and 385 at approximately equal voltages, the above-described sizing of load PFETs 405 and 406 and cascode PFETs 410 and 411 keeps the load PFETs 405 and 406 out of the nonsaturation/linear/triode region of operation. By diode-connecting cascode PFET 411, as described above, a separate bias voltage generation circuit for cascode devices 410 and 411 is not needed. In one embodiment, current mirror PFETs 391–394 and output transconductor PFET 390 are operated in the strong inversion region, and sized similarly to load PFETs 405 and 406.

As described below, the folded cascode topology of first amplifier 350 advantageously operates at a lower power supply voltage $V_{DD}$ than, for example, a conventional differential amplifier having a current mirror load. The minimum power supply voltage, $V_{DD,min}$ needed to operate first amplifier 350 is illustrated in Equation (3).

$$V_{DD,min} = V_{366} + V_{367} - V_T + \Delta V_{400} + \Delta V_{405} \quad (3)$$

In Equation (3), the minimum supply voltage, $V_{DD,min}$, is determined from: the BE voltage of diode 366, $V_{366}$, of approximately 0.5 Volts; the BE voltage of diode 367, $V_{367}$, of approximately 0.5 Volts; the process minimum threshold voltage of input NFET 400 of approximately 0.5 Volts; the minimum drain-source voltage, $\Delta V_{400}$, of approximately 0.1 Volts to keep input NFET 400 out of the nonsaturation/linear/triode region of operation; and, the minimum drain-source voltage, $\Delta V_{405}$, required to keep load FET 405 out of the nonsaturation/linear/triode region of operation, or approximately 0.2 Volts. Thus, according to Equation (3), first amplifier 350 is capable of operating from a minimum power supply voltage, $V_{DD,min}$, as low as approximately 0.8 Volts, for this biasing arrangement.

In this case, the minimum power supply voltage, $V_{DD,min}$, needed for operation of the current reference circuit 305 is not limited by the minimum power supply voltage needed for operation of first amplifier 305. Instead, the minimum power supply voltage needed for operation of current reference circuit 305 is either limited by the voltage requirements of first bias circuit 355 and its associated current mirror PFET 392, or similarly limited by the voltage requirement of second bias circuit 360 and output transconductor PFET 390. For example, the voltage requirement of first bias circuit 355 and associated current mirror PFET 392 is illustrated in Equation (4).

$$V_{DD,min} = V_{366} + V_{367} + \Delta V_{392} \qquad (4)$$

In Equation (4), the minimum power supply voltage, $V_{DD,min}$ is determined from: the BE voltage of diode 366, $V_{366}$, of approximately 0.5 Volts; the BE voltage of diode 367, $V_{367}$, of approximately 0.5 Volts; and, the minimum drain-source voltage, $\Delta V_{392}$, required to keep current mirror PFET 392 out of the nonsaturation/linear/triode region of operation, or approximately 0.25 Volts. Thus, according to Equation (4), current reference circuit 305 is capable of operating from a minimum power supply voltage, $V_{DD,min}$, as low as approximately 1.3 Volts for this biasing arrangement. In one embodiment, current reference circuit 305 is operated from a power supply voltage $V_{DD}$ that is approximately equal to 1.3 Volts. In another embodiment, current reference circuit 305 is operated at a higher power supply voltage $V_{DD}$, such as at approximately between 1.65 Volts and 3.25 Volts. It is also understood that current reference circuit 305 may be operated at even higher power supply voltages $V_{DD}$.

The value of the reference current, $I_{PTAT}$, through $R_{370}$, as described in Equation (1) represents the desired one of two possible stable operating points of current reference circuit 305. More particularly, current reference circuit 305 also has a stable operating point when $I_{PTAT}=0$. A bootstrapping function performed by startup circuit 365 ensures that current reference circuit 305 operates at the desired stable operating point described in Equation (1), and not at the undesired stable operating point of $I_{PTAT}=0$.

Startup circuit 365 is designed to establish a voltage at node 325 that turns on output transconductor PFET 390 and current mirror PFETs 391–394 such that these devices provide bias current to first and second bias circuits 355 and 360 and first amplifier 350. Startup circuit 365 is also designed to release control over the voltage at node 325 when current reference circuit 350 operates as described in Equation (1).

Startup circuit 365 comprises PFET 500, NFET 505, and pnp BJT 510. PFET 500 has a source terminal that is electrically coupled to power supply node 315, a gate terminal that is electrically coupled to node 325, and a drain terminal that is electrically coupled to the drain terminal of NFET 505 at node 515. NFET 505 has a gate terminal electrically coupled to power supply node 315 and a source terminal that is electrically coupled to ground node 320. BJT 510 has an emitter terminal that is electrically coupled to node 325, a base terminal that is electrically coupled to node 515, and a collector terminal that is electrically coupled to ground node 320.

When power is initially applied to power supply node 315, there is initially no charge on capacitor 520, hence the voltage at node 325 is approximately equal to the voltage at power supply node 315. In this first state, PFET 500 is turned off due to insufficient voltage between its gate and source terminals at nodes 325 and 315, respectively. NFET 505 is turned on, since the voltage between its gate terminal, at power supply node 315, and its source terminal, at ground node 320, is approximately equal to the power supply voltage $V_{DD}$. The voltage at node 515 is a diode voltage drop below the voltage at node 325, which is approximately equal to the voltage at power supply node 315. As a result, NFET 505 operates in a saturation region, and provides base current to BJT 510.

The collector-emitter current, $I_{CE}$, of BJT 510 charges capacitor 520 to decrease the voltage at node 325 from its initial value at approximately $V_{DD}$ until PFET 500, output transconductor PFET 390, and current mirror PFETs 391–395 turn on. In this second state, current reference circuit 305 establishes operation at the stable operating point described in Equation (1). PFET 500 is designed to source more current than NFET 505 can sink under all process and supply voltage variations, hence the voltage of node 515 is increased to $V_{DD}$, and BJT 510 turns off. NFET 505 remains on, but is sized to draw an acceptably low quiescent current in this second state.

Figure 3:
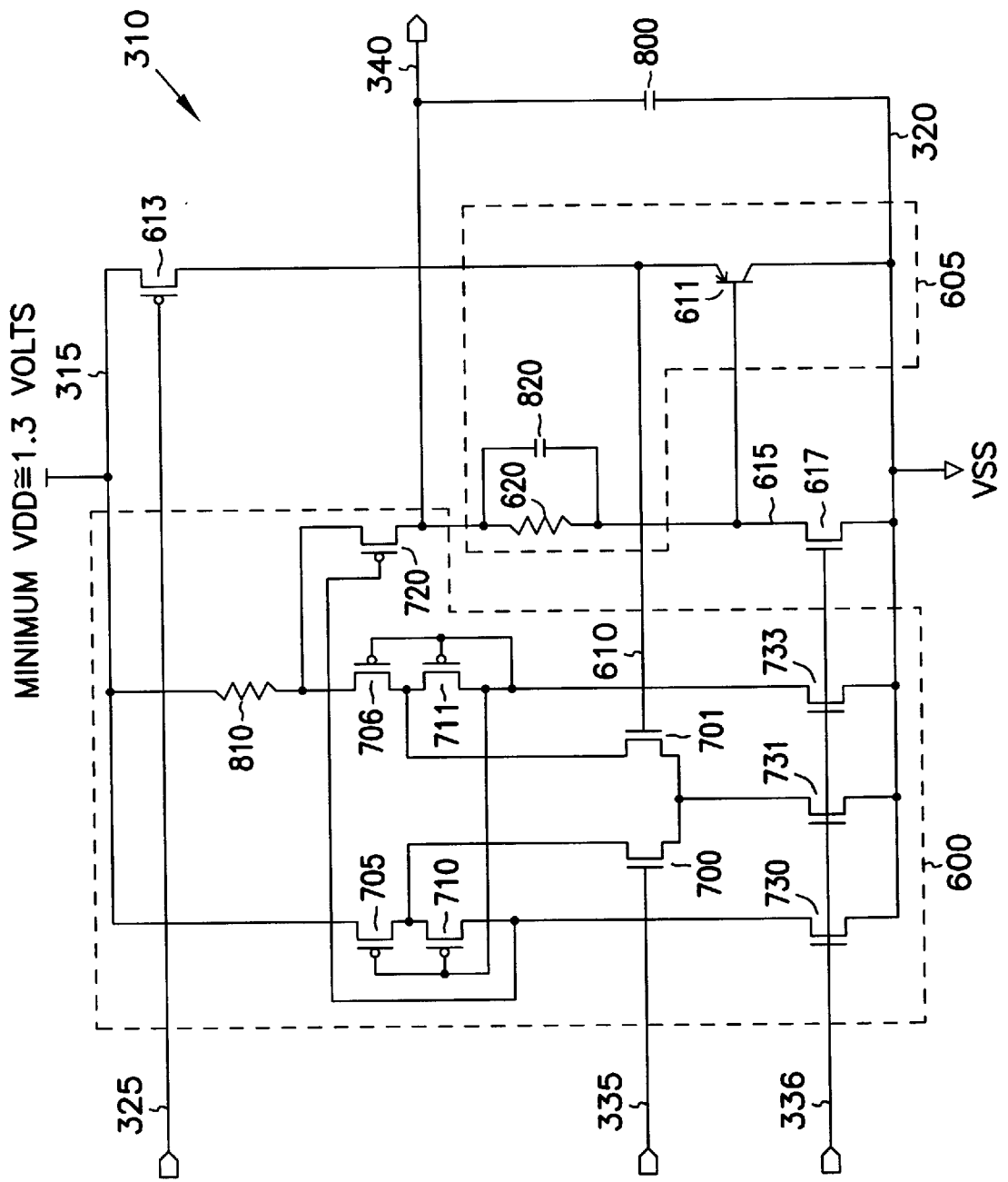
FIG. 3 is a more detailed schematic illustration of the voltage reference circuit of FIG. 1.

FIG. 3 is a more detailed schematic illustration of the voltage reference circuit 310 of FIG. 1. In FIG. 3, voltage reference circuit 310 comprises a second amplifier 600 and a third bias circuit 605. Second amplifier 600 receives at a first input at node 335 the first bias voltage, which is two series-coupled diode voltage drops above the voltage at ground node 320. Second amplifier 600 is connected in a negative feedback configuration, i.e. the output of second amplifier 600 is coupled to the inverting second input, at node 610, of second amplifier 600, through third bias circuit 605. Because second amplifier 600 is connected in a negative feedback configuration, a "virtual ground" exists between the first input, at node 335, and the second input, at node 610, of second amplifier 600, thereby providing a voltage approximately equal to the first bias voltage at its second input at node 610. Thus, the voltage at node 610 is approximately equal to two series-coupled diode voltage drops above the voltage at ground node 320. Third bias circuit 605 comprises second resistor 620, in series with diode 611, which is implemented as a BJT biased with a collector-emitter current, $I_{CE}$, received from current mirror PFET 613 having a gate terminal electrically coupled to node 325.

In third bias circuit 605, the BE voltage of diode 611 offsets the voltage at node 610 from a second voltage at node 615, such that the resulting second voltage at node 615 is approximately one diode voltage drop above the voltage at ground node 320. The temperature dependence of the second voltage at node 615 is substantially offset by the temperature dependence of a first voltage across resistor 620, which is created by the temperature dependent current provided by current mirror NFET 617. When the resistance of second resistor 620 is such that the resulting voltage at node 340 is approximately equal to the bandgap voltage of silicon, i.e. approximately 1.25 Volts, the resulting voltage at node 340 is approximately temperature compensated. In one embodiment, second resistor 620 is a variable or trimmable resistor having an adjustable resistance value $R_{620}$ near approximately 7.0 megaohms for adjusting the reference voltage at node 340 to 1.25 Volts with the desired degree of accuracy.

Second amplifier 600 is a folded-cascode amplifier designed and operating similarly to first amplifier 350, which was discussed in detail above. Second amplifier 600 comprises: input NFETs 700 and 701; load PFETs 705 and 706; output transconductor NFET 720; cascode PFETs 710 and 711; and, current mirror NFETS 730–733. Unlike first amplifier 350, second amplifier 600 is output compensated, i.e. its low frequency pole is determined, in part, by capacitor 800. Gain degeneration resistor 810, electrically coupling the common source terminals of load PFET 706 and output transconductor PFET 720 to the power supply node 315, and capacitor 820 provide improved frequency response characteristics of second amplifier 600. Second amplifier 600 stabilizes the reference voltage at node 340 and provides a load current to any other circuits that are electrically coupled to thereto.

The minimum power supply voltage, $V_{DD,min}$, needed for operation of the voltage reference circuit 310 is illustrated by Equation (5).

$$V_{DD,min} = V_{340} + \Delta V_{720} + V_{810} \qquad (5)$$

In Equation (5), the minimum power supply voltage, $V_{DD,min}$, needed for operation of the voltage reference circuit 310 is approximately limited by: the value of the reference voltage at node 340, $V_{340}$, of approximately 1.25 Volts; the minimum drain-source voltage needed for operation of output transconductor NFET 720 in the saturation region, $\Delta V_{720}$, of approximately 0.175 Volts; and, the voltage $V_{810}$, across resistor 810, which is negligible. According to Equation (5), the resulting minimum power supply voltage, $V_{DD,min}$ needed is approximately 1.45 Volts, however, as will be shown, simulation data indicates that voltage reference circuit 310 is capable of operating at an even lower power supply voltage $V_{DD,min}$.

Table 1 illustrates the performance of reference circuit 300, as obtained from a circuit simulation performed using the HSPICE Version H96.1 circuit simulator from Metasoftware, Inc., of Campbell, Calif.

TABLE 1

Operation of Reference Circuit 300 At Various Power Supply Voltages

| Power Supply Voltage $V_{DD}$ (Volts) | Reference Voltage $V_{340}$ (Volts) | Reference Current $I_{PTAT}$ at 25 degrees C. (nanoAmperes) |
|---|---|---|
| 3.250 | 1.2502 | 50.00 |
| 3.000 | 1.2518 | 50.26 |
| 2.500 | 1.2554 | 50.85 |
| 2.100 | 1.2588 | 51.41 |
| 1.450 | 1.2655 | 52.53 |
| 1.425 | 1.2658 | 52.58 |
| 1.400 | 1.2661 | 52.63 |
| 1.350 | 1.2667 | 52.73 |
| 1.325 | 1.2670 | 52.78 |
| 1.300 | 1.2673 | 52.83 |
| 1.260 | 1.2526 | 52.93 |
| 1.25 | 1.2427 | 52.96 |

The results illustrated in Table 1 indicate that current reference circuit 305 and voltage reference circuit 310 are capable of operating together from a power supply voltage $V_{DD}$ that is even lower than the 1.45 Volts yielded by Equation (5), such as a minimum power supply voltage $V_{DD,min}$ that is approximately equal to 1.3 Volts. In one embodiment, current reference circuit 305 and voltage reference circuit 310 are operated from a power supply voltage $V_{DD}$ of approximately 1.3 Volts. In another embodiment, a power supply voltage $V_{DD}$ approximately between 1.65 Volts and 3.25 Volts is used to ensure proper operation of current reference circuit 305 and voltage reference circuit 310. However, it is understood that an even higher power supply voltage $V_{DD}$ could also be used.

Figure 4:
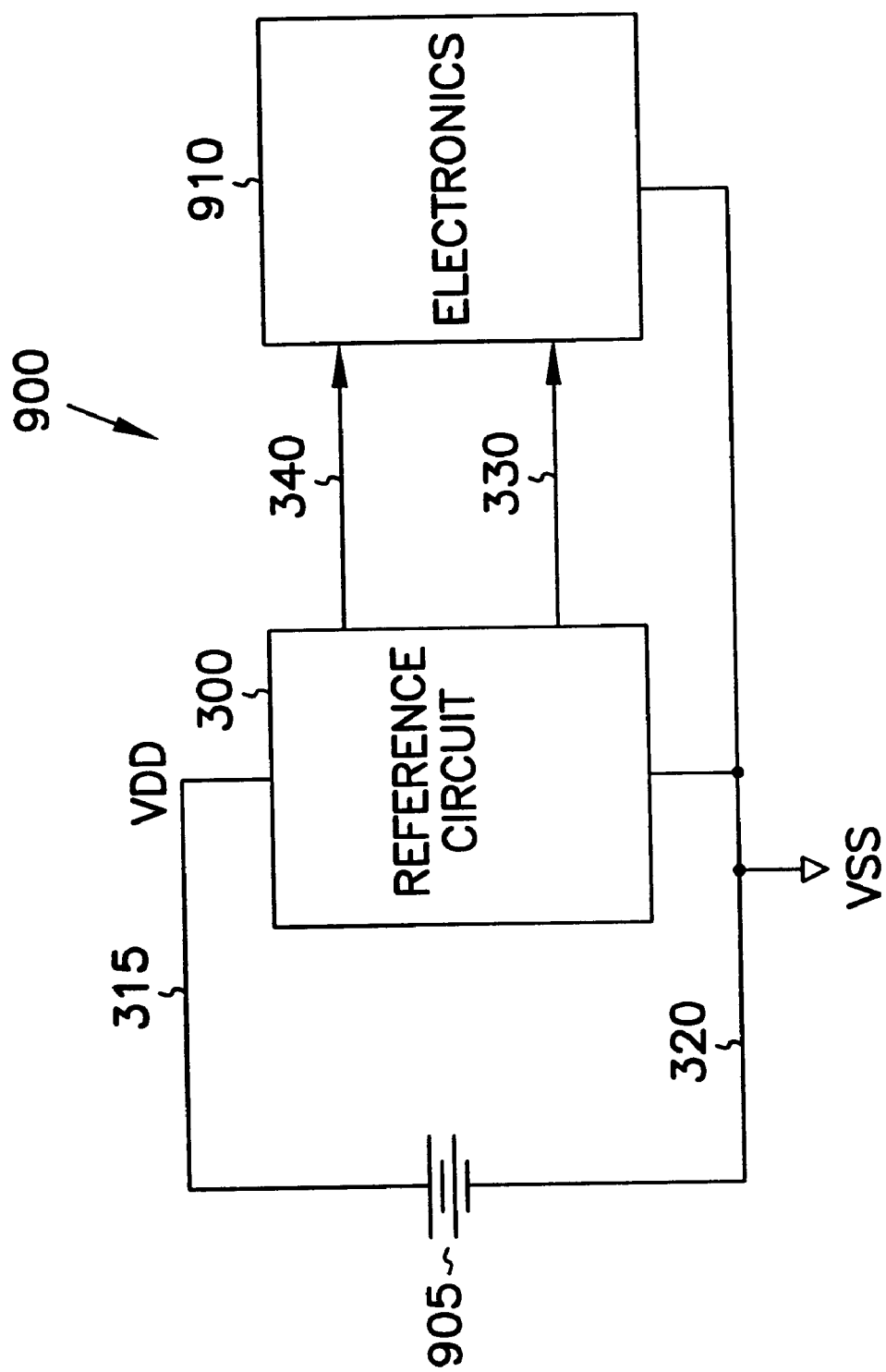
FIG. 4 is a schematic/block diagram illustrating one embodiment of the system in which the reference circuit is used in a cardiac rhythm management system.

FIG. 4 is a schematic/block diagram illustrating one embodiment of the system in which reference circuit 300 is used in a cardiac rhythm management system such as implantable cardioverter-defibrillator (ICD) 900. In one embodiment, ICD 100 includes a single lithium-silver vanadium pentoxide battery 905, providing the power supply voltage $V_{DD}$ at node 315 to reference circuit 300, and providing the ground voltage $V_{SS}$ at node 320 to reference circuit 300 and other electronics 910. Reference circuit 300 provides the reference voltage at node 340 and a current proportional to the reference current $I_{PTAT}$, through node 330, to electronics 910.

In one embodiment, the power supply voltage $V_{DD}$ provided by battery 905 is approximately equal to 3.25 Volts during time periods in which ICD 900 is monitoring a patient's heart. However, the power supply voltage $V_{DD}$ provided by the battery may drop to between approximately 1.65 Volts and 3.25 Volts while charging capacitors for providing an electrical defibrillation countershock to restore the patient's heart to a normal rhythm.

Embodiment Having Improved Power Supply Rejection

Figure 5:
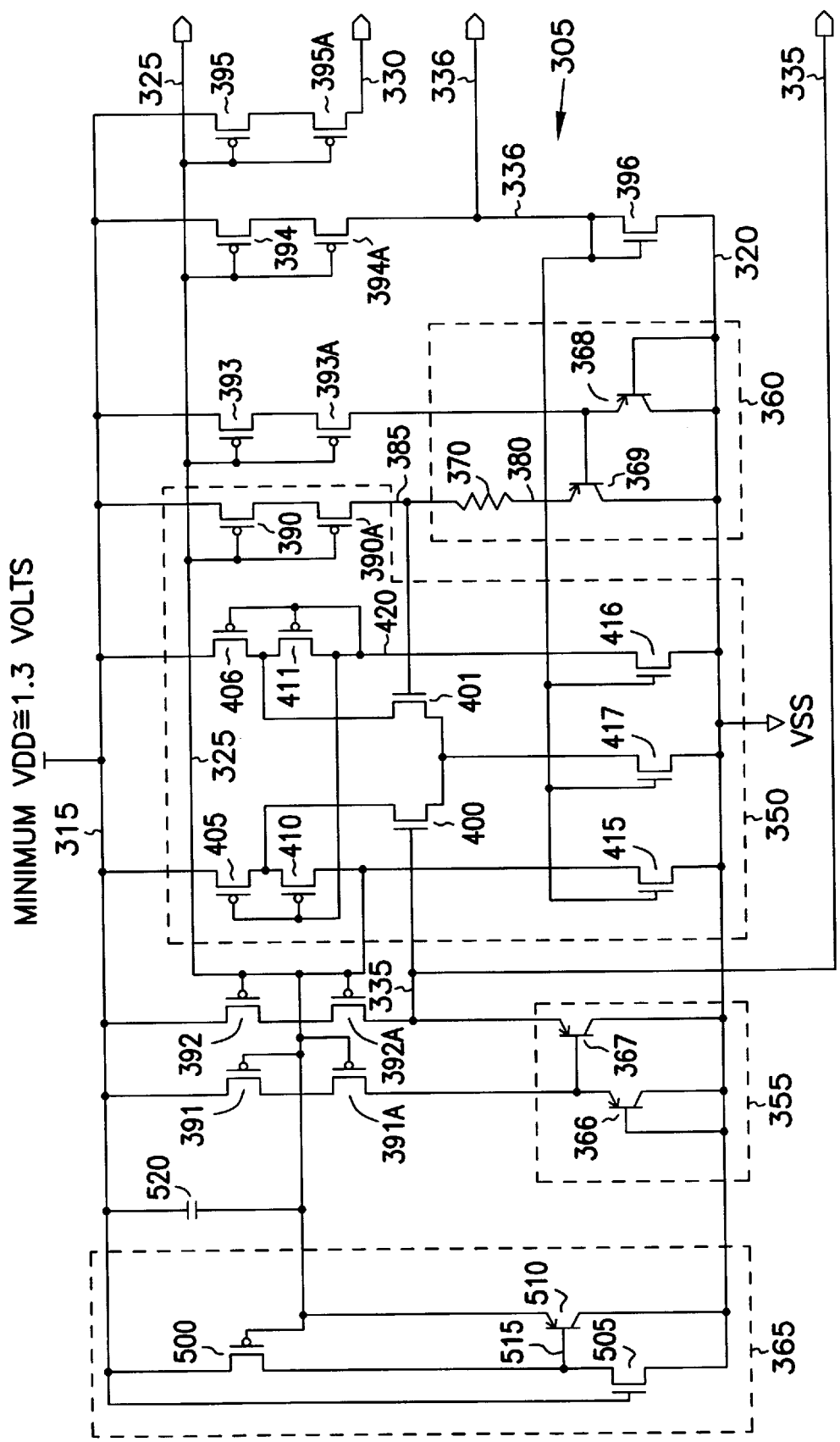
FIG. 5 is a schematic diagram, corresponding generally to FIG. 2, but providing improved power supply rejection.
Figure 6:
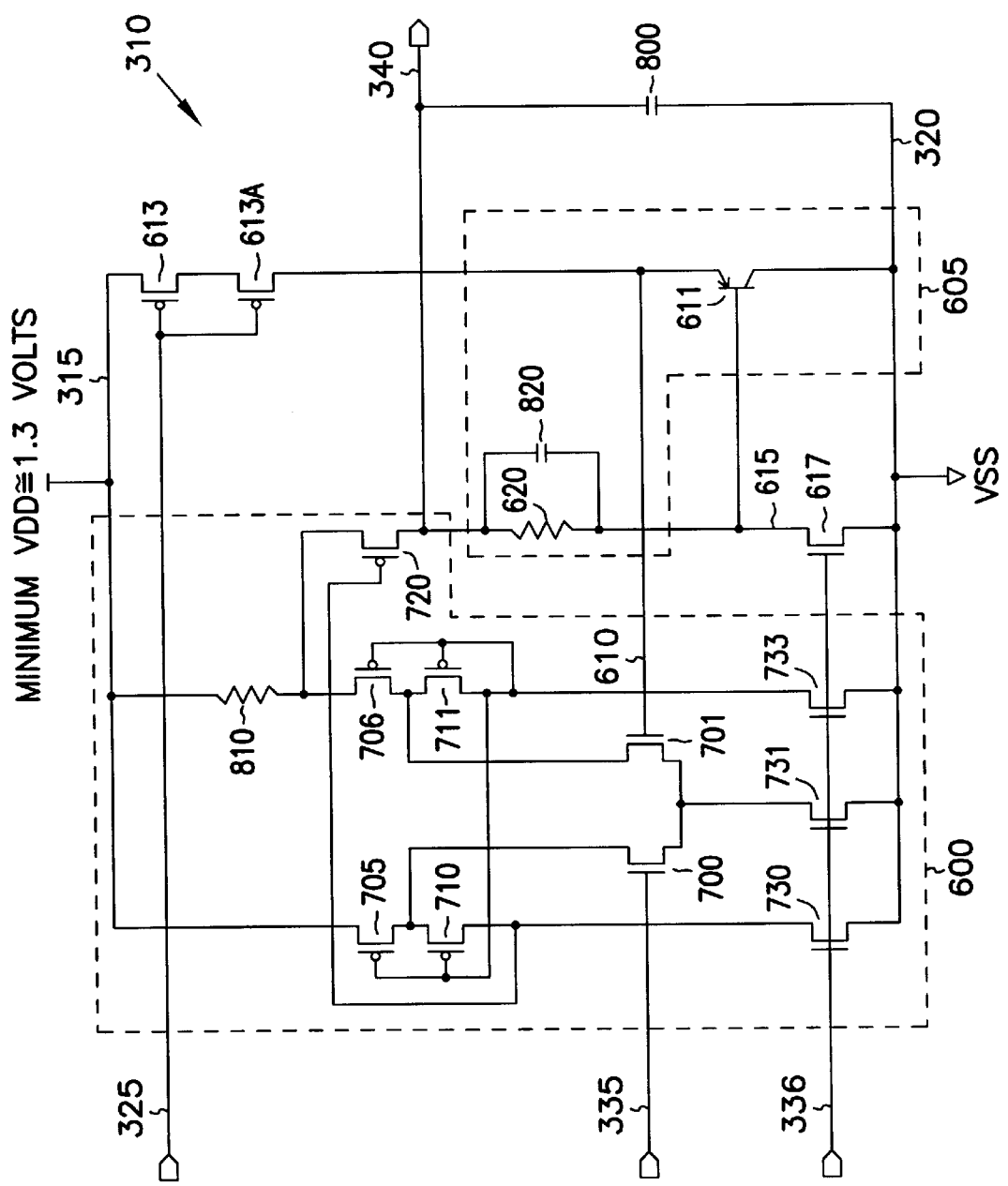
FIG. 6 is a schematic diagram, corresponding generally to FIG. 3, but providing improved power supply rejection.

FIGS. 5 and 6 are schematic diagrams, corresponding generally to FIGS. 2 and 3, respectively, but providing improved rejection to variations of the power supply line $V_{DD}$ voltage at node 315. For example, the power supply line $V_{DD}$ voltage at node 315 may droop from a value of 3.25 Volts down to a value that is close to 1.65 Volts while charging defibrillation output capacitors, as described above.

In FIGS. 5 and 6, first amplifier 350 includes a cascode-protected output device. More particularly, output transconductor PFET 390 is protected against variations in drain-to-source voltage by cascode PFET 390A. The source of cascode PFET 390A is electrically coupled to the drain of output transconductor PFET 390 such that cascode PFET 390A appears in series with output transconductor PFET 390. The gate of cascode PFET 390A is coupled to any suitable dc bias voltage such as, for example, to the gate voltage of output transconductor PFET 390 at node 325. Cascode PFET 390A reduces drain-to-source current variations in output transconductor PFET 390. Such drain-to-source current variations in output transconductor PFET 390 result from its output conductance, $g_{ds}$, together with drain-to-source voltage variations on PFET 390 due to power supply voltage $V_{DD}$ variations at node 315. Including cascode PFET 390A reduces variations in the drain-to-source voltage and current of output transconductor PFET 390.

In FIGS. 5 and 6, current mirror PFETs 391, 392, 393, 394, 395 and 613 are protected against variations in drain-to-source voltage by similarly configured respective cascode PFETs 391A, 392A, 393A, 394A, 395A and 613A. The current provided by each of cascode-protected current mirror PFETs 391, 392, 393, 394, 395 and 613 is proportional to the reference current, $I_{PTAT}$, through first resistor 370. In one embodiment, the cascode PFETs 390A, 391A, 392A, 393A, 394A, 395A and 613A are designed for operation in the weak inversion region of operation. Weak inversion operation is obtained, for example, by appropriately selecting the dimensions W and L, as described above with respect to cascode PFETs 410 and 411.

Figure 7:
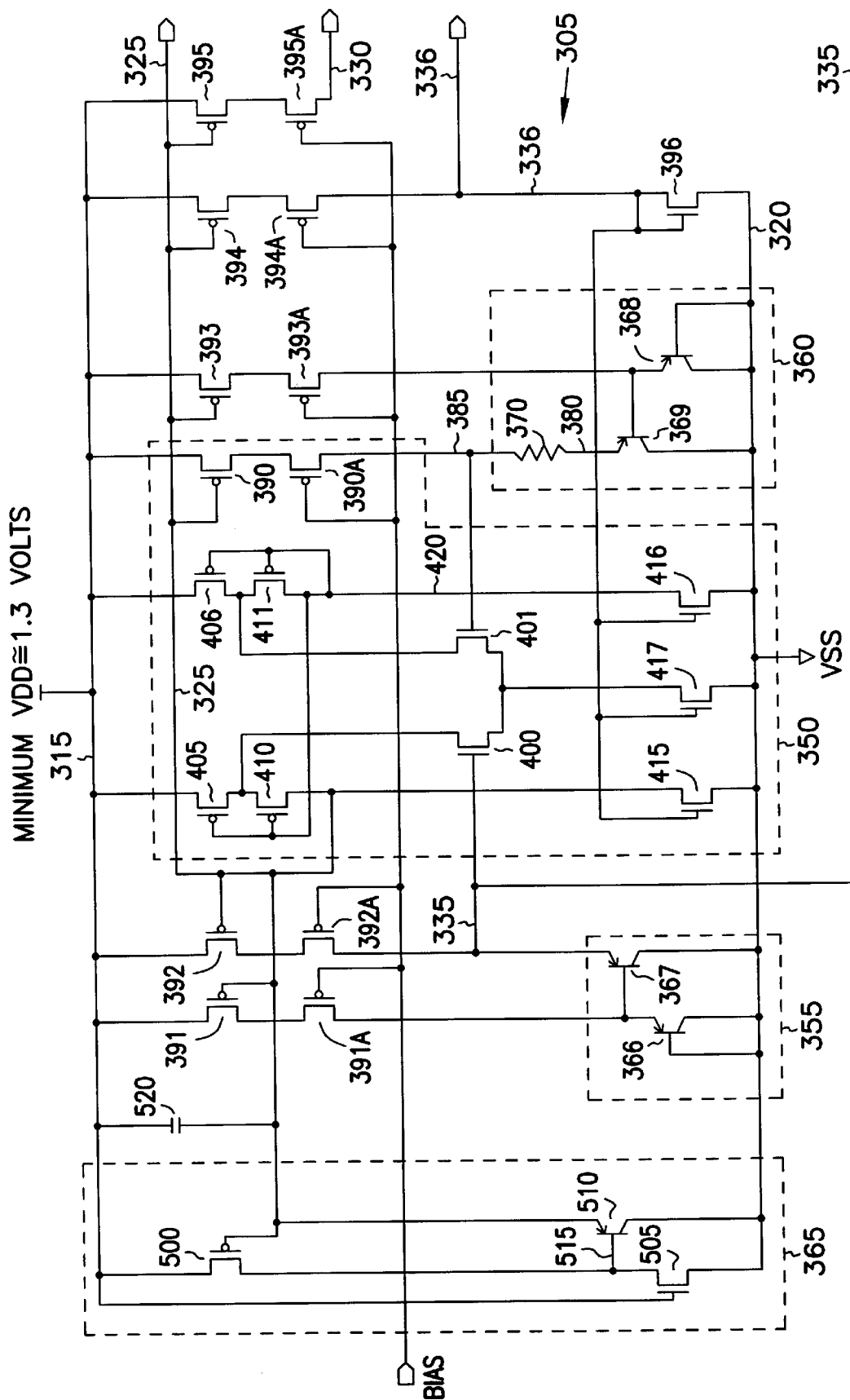
FIG. 7 is a schematic diagram, corresponding generally to FIG. 5, but using a separate bias voltage for establishing the gate voltage of the cascode devices.
Figure 8:
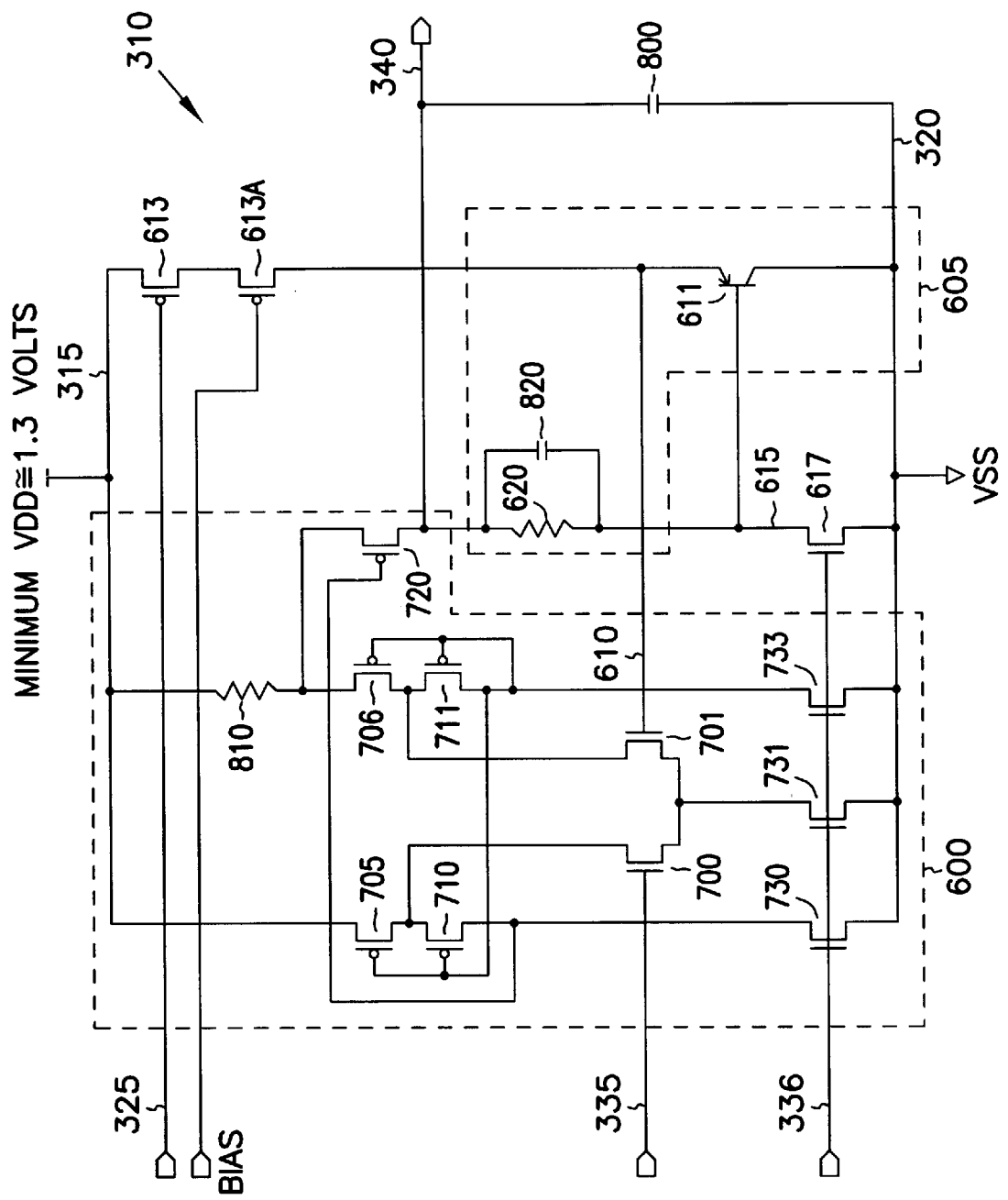
FIG. 8 is a schematic diagram, corresponding generally to FIG. 6, but using a separate bias voltage for establishing the gate voltage of the cascode devices.

FIGS. 7 and 8 are schematic diagrams, corresponding generally to FIGS. 5 and 6, respectively, but using a separate bias voltage for establishing the gate voltage of the cascode PFETs 390A, 391A, 392A, 393A, 394A, 395A and 613A. In one embodiment, for example, the bias voltage at the gates of cascode PFETs 390A, 391A, 392A, 393A, 394A, 395A and 613A is slightly more negative than the voltage at node 325.

Figure 9:
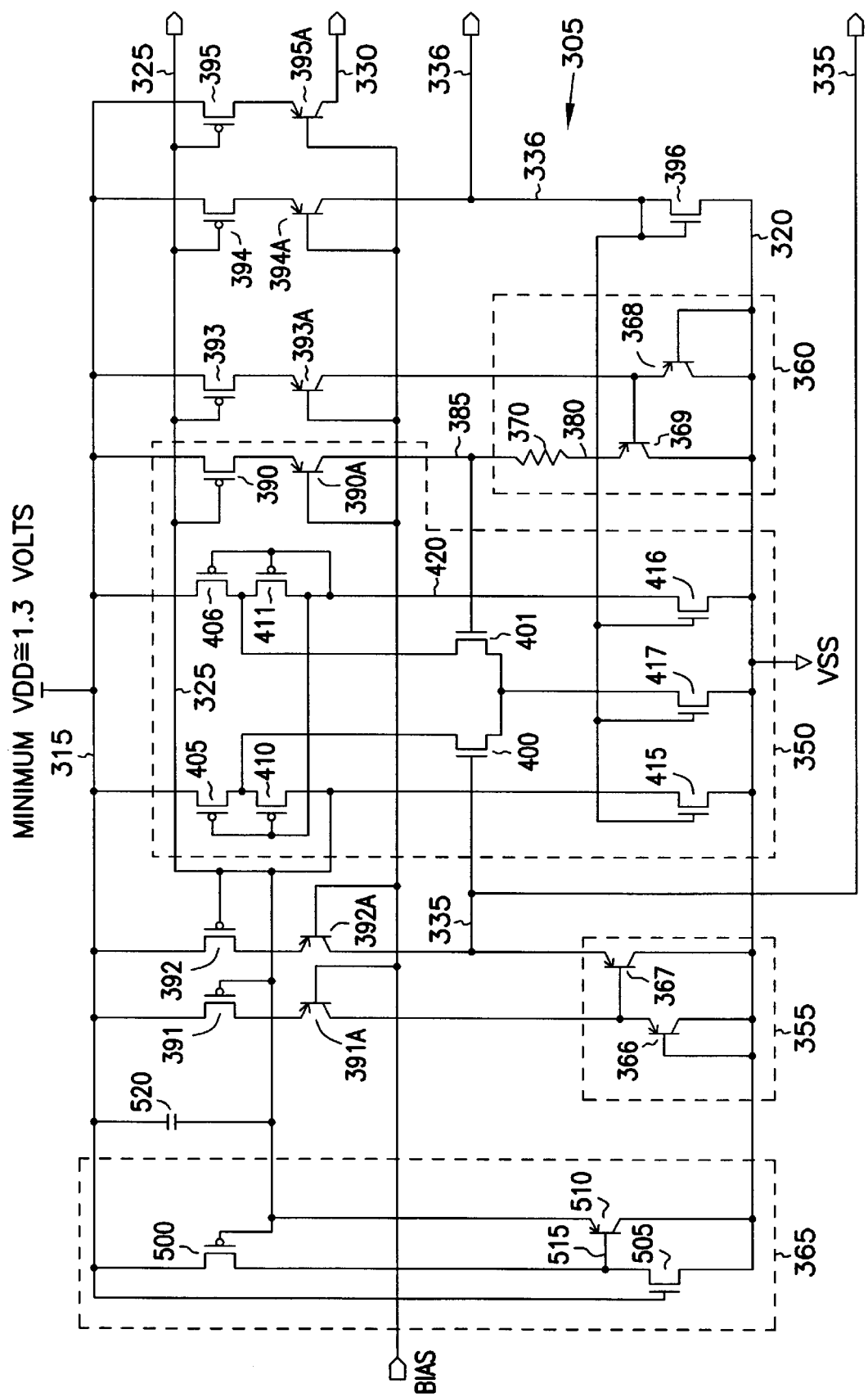
FIG. 9 is a schematic diagram, corresponding generally to FIG. 7, but using bipolar junction transistors as cascoding devices.
Figure 10:
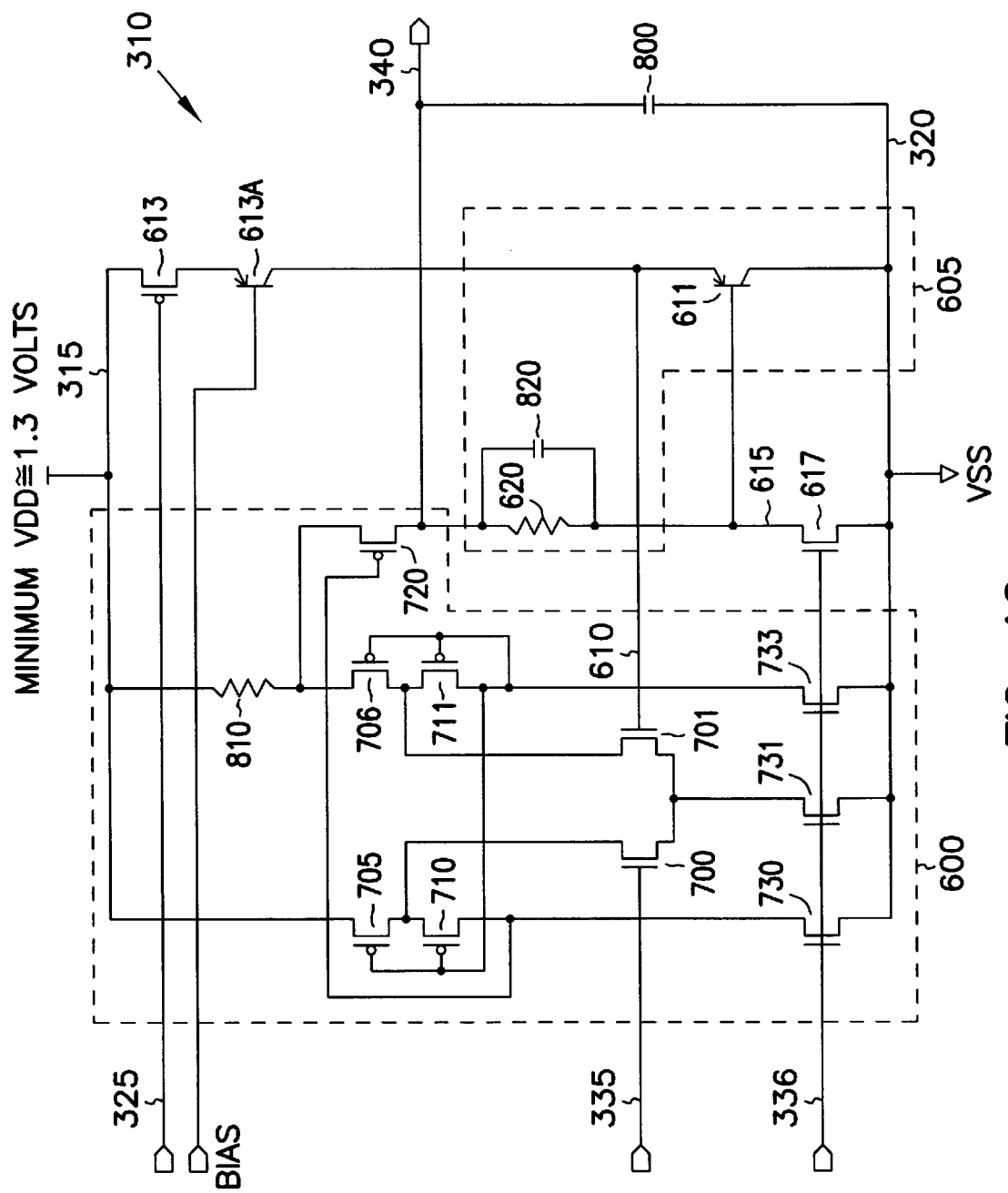
FIG. 10 is a schematic diagram, corresponding generally to FIG. 8, but using bipolar junction transistors as cascoding devices.

FIGS. 9 and 10 are schematic diagrams, corresponding generally to FIGS. 7 and 8, respectively, but using bipolar junction transistors (e.g., pnp BJTs) as cascoding devices 390A, 391A, 392A, 393A, 394A, 395A and 613A. In one embodiment, for example, the bias voltage at the bases of cascode BJTs 390A, 391A, 392A, 393A, 394A, 395A and 613A is at approximately the same voltage as node 385 (i.e., at approximately equal to two series-coupled diode voltage drops above the voltage at ground node 320). This ensures that transistors 390 and 394 have approximately the same drain voltage, improving the noise rejection of the circuit to variations of the power supply voltage at node 315.

Conclusion

For battery powered electronics applications, reference circuit 300 offers significant advantages; it may eliminate the need for electrically coupling more than one battery in series in order to obtain a higher power supply voltage. Also, in some batteries, an internal battery impedance increases over the course of the battery life, thereby reducing the voltage available at the battery terminals when appreciable currents are drawn therefrom. Thus, the useful life of the battery may be extended by using a reference circuit that is capable of operating from this reduced battery terminal voltage near the end of the battery's life. The reference circuit is also capable of accommodating such variations in the power supply voltage. This is particularly advantageous for implantable medical devices such as pacemakers and defibrillators. For example, a pacemaker may draw appreciable currents from the battery during the charging of a capacitor for the subsequent delivery of an electrical pacing pulse. In another example, a defibrillator may draw appreciable currents from the battery during the charging of a capacitor for the subsequent delivery of an electrical defibrillation countershock. Circuits that are capable of operating at reduced power supply voltages can extend battery life for several years, thereby avoiding surgical explantation and replacement of the implanted device. In elderly patients, such traumatic surgical intervention may be both uncomfortable and risky.

The system, by operating from a power supply voltage as low as approximately 1.3 Volts, may significantly increase the longevity of the implanted device in which it is used. The system also operates with low power consumption, further enhancing the longevity of the implanted device. The increased device longevity provides the implanting physician with more options in selecting the most appropriate therapy for the patient. Discomfort and patient mortality due to explantation and replacement of the implanted medical device may be decreased. The system also provides a reference circuit in which the value of the reference voltage and reference current are capable of fine adjustment. The resulting reference voltage is temperature compensated, i.e. the sensitivity of the reference voltage to temperature variations is reduced. Furthermore, improved power supply rejection better accommodates variations in the power supply voltage.

It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A reference circuit comprising:
 a first bias circuit including less than three series-coupled diodes comprising first and second series-coupled diodes biased by at least one first current source, providing a first temperature dependent voltage across the series-combination of the first and second diodes;
 a second bias circuit including a resistor and less than three series-coupled diodes comprising third and fourth series-coupled diodes biased by at least one second current source, providing a second temperature dependent voltage across the series-combination of the third and fourth diodes, wherein the second temperature dependent voltage has a different temperature dependence than the first temperature dependent voltage; and
 a complementary metal oxide semiconductor (CMOS) differential input first amplifier having first and second inputs electrically coupled to the respective first and second temperature dependent voltages of the respective first and second bias circuits, and having an output providing a proportional to absolute temperature (PTAT) reference current through the resistor by measuring a difference between the first and second temperature dependent voltages
 wherein a power supply voltage provided to the first amplifier is between 1.3 volts and 2.1 volts.

2. The reference circuit of claim 1, wherein the first amplifier is a folded-cascode amplifier.

3. The reference circuit of claim 1, wherein a power supply voltage provided to the first amplifier is as low as 1.45 Volts.

4. The reference circuit of claim 1, wherein a power supply voltage provided to the first amplifier is between 1.65 Volts and 2.1 Volts.

5. The reference circuit of claim 1, wherein the first bias circuit provides the first temperature dependent voltage of approximately 1.0 volt across the first and second series coupled diodes.

6. The reference circuit of claim 1, wherein the second bias circuit provides the second temperature dependent voltage of approximately 1.0 volt across the third and fourth series coupled diodes.

7. The reference circuit of claim 1, wherein the first and second bias circuits bias the first amplifier for operation from a power supply voltage that is between 1.45 Volts and 2.1 Volts.

8. The reference circuit of claim 1, wherein the first and second bias circuits bias the first amplifier for operation from a power supply voltage that is between 1.65 Volts and 2.1 Volts.

9. The reference circuit of claim 1, wherein at least one of the first and second diodes has a junction area that is different from that of at least one of the third and fourth diodes.

10. The reference circuit of claim 9, wherein each of the first and second diodes has a junction area that is different from that of each of the third and fourth diodes.

11. The reference circuit of claim 1, further comprising a third bias circuit, electrically coupled for receiving a current proportional to the reference current and providing a reference voltage in response thereto.

12. The reference circuit of claim 11, wherein the reference voltage is substantially temperature compensated.

13. The reference circuit of claim 12, wherein the reference voltage includes a series-combination of third and fourth voltages, in which the current proportional to the reference current establishes the third voltage having a temperature dependence that substantially offsets a temperature dependence of the fourth voltage to provide the substantially temperature compensated reference voltage.

14. The reference circuit of claim 11, further comprising a second amplifier electrically coupled to the first and third bias circuits for stabilizing the reference voltage and providing a load current.

15. The reference circuit of claim 14, wherein a power supply voltage provided to the second amplifier is between 1.3 Volts and 2.1 Volts.

16. The reference circuit of claim 14, wherein a power supply voltage provided to the second amplifier is between 1.65 Volts and 2.1 Volts.

17. The reference circuit of claim 14, wherein the first bias circuit provides the first temperature dependent voltage of approximately 1.0 volt across the first and second series coupled diodes.

18. The reference circuit of claim 14, wherein the second bias circuit provides the second temperature dependent voltage of approximately 1.0 volt across the third and fourth series coupled diodes.

19. The reference circuit of claim 1, in which the first amplifier includes a cascode-protected output transistor.

20. The reference circuit of claim 19, in which the cascode-protected output transistor provides a proportional to absolute temperature (PTAT) current.

21. The reference circuit of claim 20, in which the PTAT current is based on a PTAT reference current provided through the resistor, wherein the PTAT reference current is based on the measured difference between the first and second temperature dependent voltages.

22. The reference circuit of claim 1, in which the first amplifier is a folded-cascode amplifier and further comprising a cascode-protected first-conductivity type current mirror transistor coupled to the first amplifier.

23. The reference circuit of claim 22, further including a second conductivity type transistor having drain and gate terminals that are coupled to each other and also coupled to the cascode-protected first conductivity type current mirror transistor.

24. The reference circuit of claim 1, further including:
   a cascode-protected current source, providing a current substantially proportional to the reference current; and
   a third bias circuit, electrically coupled for receiving the current substantially proportional to the reference current from the cascode-protected current source and providing a substantially temperature compensated reference voltage in response thereto.

25. The reference circuit of claim 24, wherein the current substantially proportional to the reference current establishes a first voltage having a temperature dependence that substantially offsets the temperature dependence of a second voltage in series with the first voltage to provide the substantially temperature compensated reference voltage.

26. The reference circuit of claim 25, further comprising a second amplifier electrically coupled to the first and third bias circuits for stabilizing the reference voltage and providing a load current.

27. A cardiac rhythm management system, comprising:
   a battery;
   an electronics circuit, for controlling delivery of cardiac therapy to a patient; and
   a reference circuit, electrically coupled to the battery for receiving a first power supply voltage therefrom, and electrically coupled to a second power supply voltage, and providing a reference voltage to the electronics circuit, wherein the reference circuit operates from the first power supply voltage that is as low as 1.3 Volts, and the reference circuit includes:
      a differential amplifier;
      a first bias circuit, including less than three series-coupled diodes comprising first and second series-coupled diodes, the first bias circuit coupled to the second power supply voltage and including a first output voltage terminal for providing a first temperature dependent voltage;
      at least one first current source, that is substantially constant at a particular temperature, coupled in series between the first power supply voltage and the first output voltage terminal;
      a second bias circuit, including less than three-series-coupled diodes comprising third and fourth series-coupled diodes, the second bias circuit coupled to the second power supply voltage and including a second output voltage terminal; and for providing a second temperature dependent voltage;
      at least one second current source, that is substantially constant at a particular temperature, coupled in series between the first power supply voltage and the second output voltage terminal; and,
      wherein the first and second temperature dependent voltages are input to the differential amplifier which generates a proportional to absolute temperature current based on the difference between the first and second temperature dependent voltages.

28. A reference circuit, comprising:
   a first bias circuit, having a first temperature dependence and including less than three series-coupled diodes comprising first and second diodes that are series-coupled with each other and biased by at least a first current source, the first bias circuit providing a first temperature dependent voltage across the series combination of the first and second series-coupled diodes;
   a second bias circuit, including a resistor and less than three series-coupled diodes comprising third and fourth diodes, the third and fourth diodes being series-coupled with each other and biased by at least a second current source, the second bias circuit providing a second temperature dependent voltage across the series combination of the third and fourth series-coupled diodes, wherein the second temperature dependent voltage has a different temperature dependence than the first temperature dependent voltage;
   a CMOS differential-input folded cascode first amplifier, receiving a power supply voltage that is between 1.65 Volts and 2.1 Volts, and having first and second inputs electrically coupled to the respective first and second bias circuits, and having an output providing a proportional to absolute temperature reference current through the resistor by measuring a difference between the first and second temperature dependent voltages; and
   a voltage reference circuit, receiving a current proportional to the reference current, and providing a temperature-compensated reference voltage that is based on a series-combination of third and fourth voltages, and the current proportional to the reference current establishes the third voltage having a temperature dependence that substantially offsets the temperature dependence of the fourth voltage to provide the reference voltage.

29. A method comprising the steps of:
biasing a first bias circuit, consisting essentially of first and second diodes that are series-coupled with each other, with a first current, which is substantially constant at a particular temperature, to establish a first temperature dependent voltage and a first junction current density in the first and second diodes;

biasing a second bias circuit, consisting essentially of a resistor and third and fourth diodes, the third and fourth diodes being series-coupled with each other, with a second current, which is substantially constant at a particular temperature, to establish a second temperature dependent voltage and a second junction current density in the third and fourth diodes, the second junction current density being different than the first junction current density;

measuring a voltage difference between the first and second temperature dependent voltages; and generating a proportional to absolute temperature reference current based on the voltage difference.

30. The method of claim 29, wherein the resistance of the first resistor is adjusted to establish the predetermined desired value of the reference current at a particular temperature.

31. The method of claim 29, wherein the step of measuring the voltage difference between the first bias circuit and the second bias circuit includes using a first amplifier.

32. The method of claim 31, wherein using the first amplifier comprises using a folded-cascode amplifier.

33. The method of claim 31, wherein a power supply voltage provided to the first amplifier is as low as 1.3 Volts.

34. The method of claim 31, wherein a power supply voltage provided to the first amplifier is between 1.65 Volts and 2.1 Volts.

35. The method of claim 29, further comprising the step of providing a current that is based on the reference current to a third bias circuit to generate a temperature compensated reference voltage.

36. The method of claim 29, further comprising the step of applying a current proportional to the reference current to a third bias circuit to establish a reference voltage that is based on a series-combination of third and fourth voltages, the third voltage having a temperature dependence that substantially offsets the temperature dependence of the fourth voltage.

37. The method of claim 36, wherein applying the current includes applying the current through a second resistor, across which the third voltage is established.

38. The method of claim 36, further comprising the step of establishing the resistance of the second resistor to establish the value of the third voltage such that is substantially offsets the temperature dependence of the fourth voltage.

39. A reference circuit, comprising:

a first power supply providing a voltage that is between 1.3 volts and 2.1 volts;

a first bias circuit including less than three series-coupled diodes comprising first and second series-coupled diodes biased by at least one first current source, providing a first temperature dependent voltage across the series-combination of the first and second series-coupled diodes;

a second bias circuit including less than three series-coupled diodes comprising a resistor, and also comprising third and fourth series-coupled diodes biased by a second current source, providing a second temperature dependent voltage across the third and fourth series-coupled diodes, wherein the second temperature dependent voltage has a different temperature dependence than the first temperature dependent voltage; and a complementary metal-oxide-semiconductor (CMOS) differential input first amplifier, the first amplifier including:

a first input transistor, having a drain and a source, and having a gate coupled to the first bias circuit;

a second input transistor, having a drain, a source coupled to the source of the first input transistor, and a gate coupled to the second bias circuit;

a first load transistor, having a source coupled to the first power supply, a drain coupled to the drain of the first input transistor, and a gate;

a second load transistor, having a source coupled to the first power supply, a drain coupled to the drain of the second input transistor, and a gate coupled to the gate of the first load transistor;

a first load cascode transistor, having a source coupled to the drain of the first load transistor, a drain, and a gate coupled to the gate of the first load transistor;

a second load cascode transistor, having a source coupled to the drain of the second load transistor, a drain, and a gate coupled to the gate of the second load transistor;

a third load transistor, having a drain coupled to the drain of the first load cascode transistor, a gate, and a source coupled to a second power supply;

a fourth load transistor, having a drain coupled to the drain of the second load cascode transistor, a gate, and a source coupled to the second power supply; and an output transistor, having a source coupled to the first power supply, a drain, and a gate coupled to the drain of the first load cascode transistor.

40. The reference circuit of claim 39, further including:

an output cascode transistor, series-connected between the drain of the output transistor and the second bias circuit, and wherein the output transistor provides a proportional to absolute temperature (PTAT) reference current through the output cascode transistor and the resistor by measuring a difference between the first and second temperature dependent voltages.

41. The reference circuit of claim 40, in which the output cascode transistor includes an output field-effect transistor (FET) having a source coupled to the drain of the output transistor, a drain coupled to the second bias circuit, and a gate coupled to a first bias voltage.

42. The reference circuit of claim 41, in which the first bias voltage is provided by the drain of the first load cascode transistor.

43. The reference circuit of claim 40, in which the output cascode transistor includes a pnp output bipolar junction transistor (BJT) having an emitter coupled the drain of the output transistor, a collector coupled to the second bias circuit, and a gate coupled to a first bias voltage.

44. The reference circuit of claim 43, in which the first bias voltage is approximately two diode voltage drops more positive than a voltage of the second power supply.

45. The reference circuit of claim 39, further comprising:

a first current mirror transistor having a source coupled to the first power supply, a drain, and a gate coupled to the gate of the output transistor; and a first current mirror cascode transistor having a source coupled to the drain of the first current mirror transistor, a drain, and a gate coupled to a second bias voltage.

46. The reference circuit of claim 45, in which the second bias voltage is provided by the drain of the first load cascode transistor.

47. The reference circuit of claim 45, further comprising a diode-connected transistor having a source coupled to the second power supply, and a drain and a gate, each of the drain and gate of the diode-connected transistor being coupled to the drain of the first current mirror cascode transistor.

48. The reference circuit of claim 47, wherein the drain and gate of the diode-connected transistor are each coupled to the gate of the third load transistor.

49. The reference circuit of claim 45, further comprising:
a second current mirror transistor having a source coupled to the first power supply, a drain, and a gate coupled to the gate of the output transistor;
a second current mirror cascode transistor having a source coupled to the drain of the second current mirror transistor, a drain providing a current substantially proportional to the reference current, and a gate coupled to a third bias voltage; and
a third bias circuit, electrically coupled to the drain of the second current mirror cascode transistor for receiving the current substantially proportional to the reference current and providing a substantially temperature compensated reference voltage in response thereto.

50. The reference circuit of claim 49, wherein the current substantially proportional to the reference current establishes a first voltage having a temperature dependence that substantially offsets the temperature dependence of a second voltage in series with the first voltage to provide the substantially temperature compensated reference voltage.

51. The reference circuit of claim 50, further comprising a second amplifier electrically coupled to the first and third bias circuits for stabilizing the reference voltage and providing a load current.

52. A reference circuit, comprising:
a first bias circuit including less than three series-coupled diodes comprising first and second series-coupled diodes biased by a first current source, providing a first temperature dependent voltage across the series-combination of the first and second series-coupled diodes;
a second bias circuit including a resistor and also including less than three series-coupled diodes comprising third and fourth series-coupled diodes biased by a second current source, providing a second temperature dependent voltage across the series-combination of the third and fourth series-coupled diodes, wherein the second temperature dependent voltage has a different temperature dependence than the first temperature dependent voltage;
a folded cascode complementary metal-oxide-semiconductor (CMOS) differential input first amplifier, receiving a power supply voltage approximately between 1.3 Volts and 2.1 Volts, and having first and second inputs electrically coupled to the respective first and second bias circuits, and having an output transistor providing a proportional to absolute temperature (PTAT) reference current through the resistor by measuring a difference between the first and second temperature dependent voltages;
a cascode-protected current source, providing a current substantially proportional to the reference current; and
a voltage reference circuit, receiving the current substantially proportional to the reference current from the cascode-protected current source, and providing a first voltage having a temperature dependence that substantially offsets the temperature dependence of a second voltage in series with the first voltage to provide a resulting temperature compensated reference voltage.

53. The reference circuit of claim 52, in which the output transistor is cascode protected.

* * * * *